United States Patent [19]

Wiegner et al.

[11] 4,217,900
[45] Aug. 19, 1980

[54] MENSTRUATION TAMPON

[75] Inventors: Georg Wiegner, Viersen; Hartmut Schwolow, Grefrath; Dieter Klein, Erkelenz; Jürgen Malaskiewicz, Dusseldorf, all of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 948,220

[22] Filed: Oct. 3, 1978

[30] Foreign Application Priority Data

Oct. 3, 1977 [DE] Fed. Rep. of Germany ....... 2744466

[51] Int. Cl.² ............................................ A61F 13/20
[52] U.S. Cl. ................................................... 128/285
[58] Field of Search ............... 128/284, 285, 287, 290, 128/296, 270

[56] References Cited

U.S. PATENT DOCUMENTS

| 3,055,369 | 9/1962 | Graham, Jr. ........................ 128/285 |
| 3,359,981 | 12/1967 | Hochstrasser ....................... 128/285 |
| 3,976,075 | 8/1976 | Chinai et al. ........................ 128/285 |
| 3,994,298 | 11/1976 | Des Marais ......................... 128/285 |
| 4,044,766 | 8/1977 | Kaczmarzyk et al. ............... 128/285 |
| 4,105,033 | 8/1978 | Chatterjee et al. .................. 128/285 |

FOREIGN PATENT DOCUMENTS 827838  6/1952  Fed. Rep. of Germany ........... 128/285

Primary Examiner—C. Fred Rosenbaum
Attorney, Agent, or Firm—Hammond & Littell, Weissenberger and Muserlian

[57] ABSTRACT

A menstruation tampon of wadding of cotton or rayon staple fibers with a treatment for increased absorbency by addition of a hydrophilic agent including fibers treated with said hydrophilic agent, in the form of a rolled tampon having the improvement wherein the wadding contains an increased proportion of said hydrophilic agent deposited on a longitudinal section which is relatively short in relation to the length of the tampon, which acts as an absorbency reservoir.

4 Claims, 7 Drawing Figures

MENSTRUATION TAMPON

BACKGROUND OF THE INVENTION

As a rule, tampons consist of mixtures of cotton and rayon staple wadding in rolled form. They are produced in different sizes, that is, quantities of wadding material, and consequently also have different absorption capacities. What determines the quality of a menstruation tampon is its absorbency.

There are substances which in admixtures with the wadding greatly improve the absorption capacity of the fiber. These substances are hydrophilic agents and include, for example, carboxymethyl cellulose (CMC). Similar effects can be obtained also with other substances which have special sorptive properties, such as certain hydrophilic polymers or foamed polyurethanes. By sprinkling such substances, such as carboxymethyl cellulose fibers (CMC fibers) onto the wadding surface, the absorption capacity of the entire tampon can be increased appreciably. For example, 5% admixtures result in 15% to 20% improvements of the absorption capacity.

A tampon with a fiber admixture modified to be more hydrophilic is known, for example, from German Published Application DOS No. 2,614,122. The fiber admixture is here distributed uniformly over the entire tampon. While the tampon has a very good absorbency, it does not have an absorption reserve when fluid occurs suddenly.

To form such zones, which serve to improve the rate of absorption and absorption capacity for the purpose of preventing the bleeding through past the tampon, amplified zones of wadding have heretofore been used. It was found, however, that with appreciable zone-wise amplification of the amount of wadding, overpressures in the tampon are inevitable, whereby the absorption capacity is greatly reduced.

OBJECTS OF THE INVENTION

It is an object of the invention to provide a tampon of the above-mentioned kind which has, in addition to a normal good absorbency, an absorption reserve to take care of a sudden occurrence of fluid.

Another object of the present invention is the development of a menstruation tampon of wadding from fibers selected from the group consisting of cotton fibers, rayon staple fibers and mixtures thereof, said wadding having been treated to give increased absorbency by addition of a hydrophilic agent and rolled into a tampon, the improvement wherein said wadding contains an increased proportion of said hydrophilic agent deposited on a longitudinal section which is relatively short in relation to the length of the formed tampon, which forms a zone of increased absorbency.

These and other objects of the invention will become more apparent as the description thereof proceeds.

THE DRAWINGS

DESCRIPTION OF THE INVENTION

Figure 1:
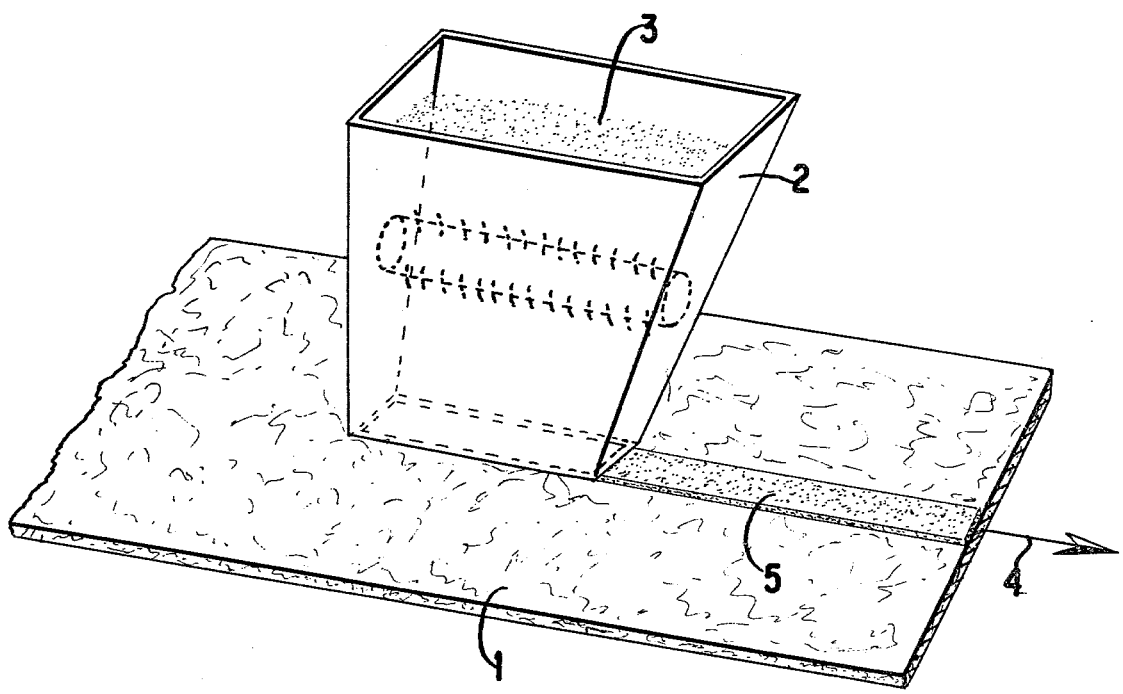
FIG. 1 is a perspective view showing the deposition of the hydrophilic agent on the length of wadding.

The drawbacks of the prior art can be overcome and the above objects can be achieved by a menstruation tampon construction wherein, on a longitudinal section of the tampon which is relatively short in relation to its length, the wadding contains at the end, in the center, or at the head of the tampon, an increased proportion of the hydrophilic agent which improves the absorption of the wadding.

More particularly, the present invention relates to the improvement of a menstruation tampon of wadding from fibers selected from the group consisting of cotton fibers, rayon staple fibers and mixtures thereof, said wadding having been treated to give increased absorbency by addition of a hydrophilic agent and rolled into a tampon, the improvement wherein said wadding contains an increased proportion of said hydrophilic agent deposited on a longitudinal section which is relatively short in relation to the length of the formed tampon, which forms a zone of increased absorbency.

Due to the fact that, according to the invention, especially absorbent substances are incorporated by controlled application in a narrow horizontal zone in the rolled tampon, there result upon use clearly visible diameter increases in the tampon and appreciable improvements in volume absorbed in the area of this especially absorbent zone. And because, according to further invention, it suffices to add to the absorbent longitudinal sections of the tampon about 2% to 5% by weight of the hydrophilic agent admixture which improves the absorbency of the wadding, overpressures (reducing the absorbency) cannot occur in the tampon. As a rule, it may lastly be favorable additionally to add to the total wadding used for making the tampon a small quantity of the hydrophilic agent admixture in question. But this quantity should be small in relation to that contained in the absorbent zones intended as absorption reserve.

The longitudinal section of the rolled tampon containing the from 2% to 5% by weight of the hydrophilic agent admixture which section is relatively short in relation to the length of the formed or rolled tampon, is usually from 10% to 35%, preferably from 15% to 30% and most particularly from 17% to 25%, of the total length of the formed or rolled tampon. The rolled or formed tampon is at least a double thickness of the wadding band on which the hydrophilic agent admixture is deposited. Therefore, while the width of the longitudinal section along the width of the wadding band on which the hydrophilic agent admixture is deposited remains the same as above, the width of the wadding band is greater and the percentage of the longitudinal section with reference to the total width of the wadding band is considerably less.

In the method of manufacturing the menstruation tampon according to the invention, the preferred procedure is to prepare a moving wadding band which preferably is already calendered and optionally contains a basic amount over its entire width of the hydrophilic agent admixture, in the range of 0.5% to 3% by weight. The hydrophilic agent admixture which improves absorbency is then scattered along a line parallel to the longitudinal direction of the moving wadding band, in a strip thereof which is narrow in comparison to the width of the wadding band, as discussed above. Then the deposited hydrophilic agent admixture strip is sealed by folding the edges of the wadding band. The folded wadding band is then pressed or calendered and deposited in rolls, where the accumulative thickness of the hydrophilic agent admixture deposit causes a bulge at the area of the rolled strip. Thereafter, the final tampon is formed from lengths of the folded wadding band by rolling.

Figure 2:
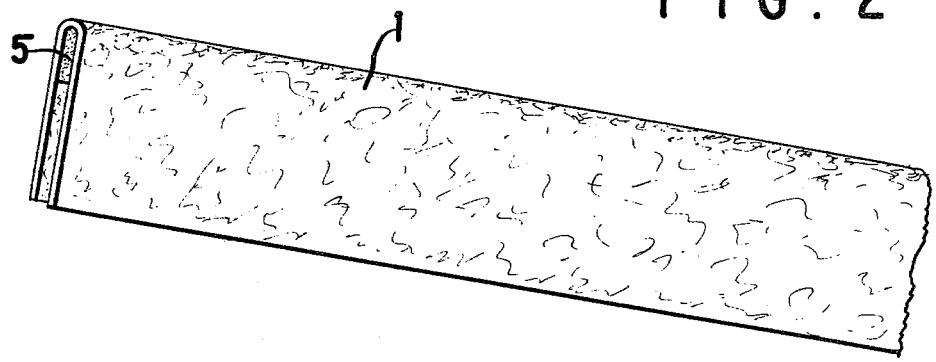
FIG. 2 shows a length of wadding folded once.
Figure 3:
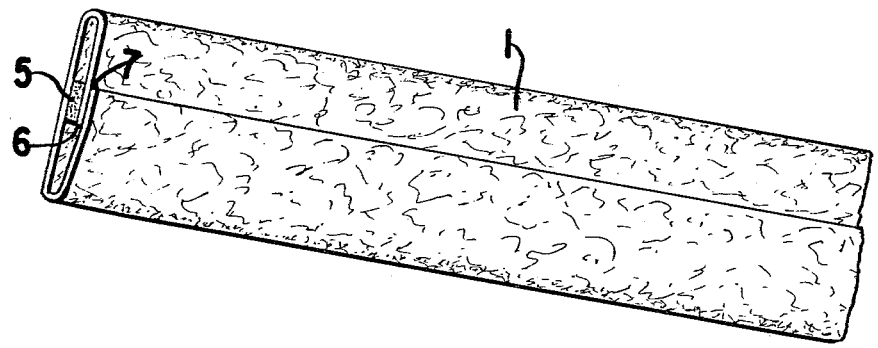
FIG. 3 shows a length of wadding folded twice.
Figure 4:
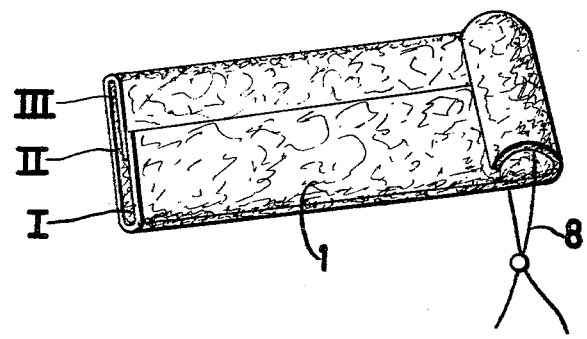
FIG. 4 shows a length of wadding folded twice in the process of being rolled.

Further details of the invention will be explained with reference to the diagrammatic drawing, showing:

FIG. 1, the application of the hydrophilic agent admixture on a wadding band;

FIG. 2, a wadding band folded once;

FIG. 3, a wadding band folded twice;

FIG. 4, a tampon when being rolled up; and

Figure 5:
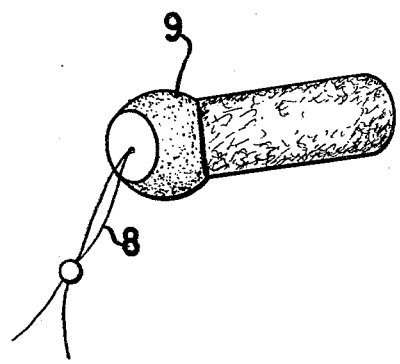
FIGS. 5 to 7 show a perspective view of three different embodiments of the menstruation tampon of the invention.
Figure 6:
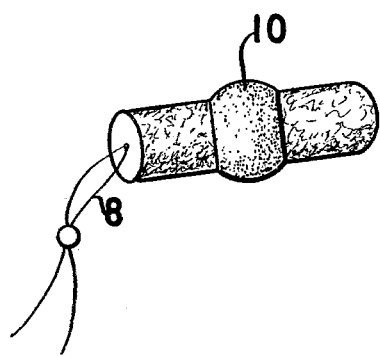
Figure 7:
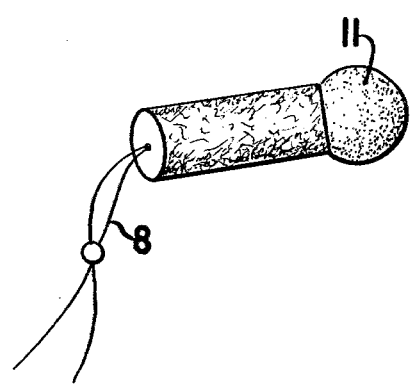

FIGS. 5 to 7, three tampons with the absorption zone of the invention at the end, in the center, or at the head.

In the manufacture of the menstruation tampon of the invention, first the wadding 1 is prepared by means of a common wadding card. The fibers of the wadding can be loaded, as desired, with a base load of the hydrophilic agent admixture or the same possibly can be scattered onto the wadding band. Following this card, a calendering station is provided, which makes a wadding band corresponding to twice the width of the wadding band later fed into the tampon machine.

Above this wadding band 1 is, according to FIG. 1, a willowing or proportioning device 2 for applying the said hydrophilic agent admixture 3. The admixture is scattered on the wadding band 1 continuously as the wadding band 1 runs in arrow direction 4, depending on where it is wanted, in narrow strips 5 in the direction of flow.

After the hydrophilic agent admixture 3 has been applied, the wadding band 1 is folded to its final format according to FIG. 2 or 3. In so doing, the hydrophilic agent admixture strip 5 is expediently sealed into the overlapping portion of the wadding band, to prevent subsequent spilling. It may be favorable to make a double fold, according to FIG. 3, by flapping both longitudinal edges 6 and 7 of the wadding band over by 180 degrees and placing them one on the other. After the folding, pressing is again effected, for example, by means of a goffered or plain calender, followed by delivery of the folded wadding band 1 into rolls or cans.

In this manner it is possible to provide especially absorbent zones serving as absorption reserve at any desired point of the tampon, which zones later become stacked during winding of the wadding band into the tampon in an enlarged zonal area; in other words, spaced at the thickness of the wadding band. It is thus possible to obtain relatively highly condensed absorption zones which, nevertheless, because of the special properties of the hydrophilic agent admixture in question, of the CMC fiber, do not lead to any appreciable increases of the pressing pressure in the tampon machine. Hence, there is no danger of overpressing.

In FIG. 4 are shown schematically three alternative positions I, II and III of the strip 5 (FIG. 1) consisting of the hydrophilic agent admixture 3 within a wadding band 1 folded according to FIG. 3. Further, it is evident from FIG. 4 how the removal cord or pull string 8 can be rolled into the tampon as the latter is being coiled or rolled.

FIGS. 5 to 7 correspond in sequence to the strip positions I, II and III of FIG. 4. Therefore, if the strip 5 of the hydrophilic agent admixture arranged according to the invention inside the tampon in a concentrated form has the position I in FIG. 4, there results, according to FIG. 5, a condensed absorption zone 9 at the end of the tampon. If, however, the strip 5 has the position II in FIG. 4, the condensed absorption zone 10, according to FIG. 6, is situated in the center of the tampon. Lastly, if the strip 5 of the hydrophilic agent admixture has been scattered on at the location III of FIG. 4, the condensed absorption zone 11 lies at the head of the tampon.

Tests have shown that the optimum absorption zones can be obtained with quantities of 2% to 5% of the hydrophilic agent admixture, for example, carboxymethyl cellulose. Similar percentual proportions apply to other substances, for example, hydrophilic polymers or foamed polyurethanes, having special absorption properties, which can be used to improve the absorbency of wadding.

The preceding embodiments are illustrative of the practice of the invention. It is to be understood, however, that other expedients known to those skilled in the art, or disclosed herein, may be employed without departing from the spirit of the invention or the scope of the appended claims.

We claim:

1. A menstruation tampon of wadding from fibers selected from the group consisting of cotton fibers, rayon staple fibers and mixtures thereof, said wadding having been treated to give increased absorbing by addition of from 0.5% to 3% by weight of a hydrophilic agent evenly dispersed on said wadding and rolled into a tampon, said wadding further containing from 2% to 5% by weight of a hydrophilic agent deposited on a longitudinal section which is from 10% to 35% of the total length of the formed tampon, which forms a zone of increased absorbency.

2. The menstruation tampon of claim 1 wherein said longitudinal section is from 15% to 30% of the total length of said tampon.

3. The menstruation tampon of claim 1 wherein said longitudinal section is from 17% to 25% of the total length of said tampon.

4. The menstruation tampon of claim 1 wherein said hydrophilic agent is carboxymethyl cellulose fibers.

* * * * *